(12) United States Patent
Kim et al.

(10) Patent No.: US 8,969,537 B2
(45) Date of Patent: Mar. 3, 2015

(54) **SINGLE-STRANDED NUCLEIC ACID APTAMERS SPECIFICALLY BINDING TO *E. COLI***

(71) Applicant: Korea Institute of Science and Technology, Seoul (KR)

(72) Inventors: Byoung Chan Kim, Seoul (KR); Yeon Seok Kim, Seoul (KR); Jong Soo Jurng, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 285 days.

(21) Appl. No.: 13/752,662

(22) Filed: Jan. 29, 2013

(65) Prior Publication Data
US 2014/0045192 A1    Feb. 13, 2014

(30) Foreign Application Priority Data

Aug. 7, 2012    (KR) .................. 10-2012-0086395

(51) Int. Cl.
*C07H 21/02*    (2006.01)
*C12M 1/34*    (2006.01)
*C12N 15/115*    (2010.01)
*G01N 33/569*    (2006.01)

(52) U.S. Cl.
CPC ........ *C12N 15/115* (2013.01); *G01N 33/56911* (2013.01); *G01N 33/56916* (2013.01); *G01N 2333/245* (2013.01)
USPC ...................................... 536/23.1; 435/287.2

(58) Field of Classification Search
USPC ...................................... 435/287.2; 536/23.1
See application file for complete search history.

(56) References Cited

FOREIGN PATENT DOCUMENTS

KR    10-0730359    6/2007

OTHER PUBLICATIONS

Korean Office Action mailed Jan. 6, 2014 in corresponding Korean Application No. 10-2012-0086395.

*Primary Examiner* — Jon E Angell
(74) *Attorney, Agent, or Firm* — Goldilocks Zone IP Law (57) ABSTRACT

Provided are a single-stranded nucleic acid aptamer specifically binding to *E. coli* and a method for detecting *E. coli* using the same. The method, kits or sensors of the present disclosure enable *E. coli* to be specifically detected among microorganisms existing in a water system, but also be applied in fields such as food sanitation or medical diagnosis.

10 Claims, 8 Drawing Sheets

SEQUENCE LISTING

```
<160> NUMBER OF SEQ ID NOS: 31

<210> SEQ ID NO 1
<211> LENGTH: 45
<212> TYPE: DNA
<213> ORGANISM: Artificial sequence
<220> FEATURE:
<223> OTHER INFORMATION: aptamer

<400> SEQUENCE: 1
acttaggtcg aggttagttt gtcttgctgg cgcatccact gagcg            45

<210> SEQ ID NO 2
<211> LENGTH: 45
<212> TYPE: DNA
<213> ORGANISM: Artificial sequence
<220> FEATURE:
<223> OTHER INFORMATION: aptamer

<400> SEQUENCE: 2
ccatgagtgt tgtgaaatgt tgggacacta ggtggcatag agccg             45

<210> SEQ ID NO 3
<211> LENGTH: 45
<212> TYPE: DNA
<213> ORGANISM: Artificial sequence
<220> FEATURE:
<223> OTHER INFORMATION: aptamer

<400> SEQUENCE: 3
aggttcgaac gtcatgatgc cccagttgac atcattcaaa cggat             45

<210> SEQ ID NO 4
<211> LENGTH: 45
<212> TYPE: DNA
<213> ORGANISM: Artificial Sequence
<220> FEATURE:
<223> OTHER INFORMATION: aptamer

<400> SEQUENCE: 4
tgttcgtcgc cgcgtggcct gggggagggg ttgcttgatt gccta             45

<210> SEQ ID NO 5
<211> LENGTH: 45
<212> TYPE: DNA
<213> ORGANISM: Artificial Sequence
<220> FEATURE:
<223> OTHER INFORMATION: aptamer

<400> SEQUENCE: 5
ccactgcggt tggcgcgccg acctttctgt tagcctgaaa cgcag             45

<210> SEQ ID NO 6
<211> LENGTH: 45
<212> TYPE: DNA
<213> ORGANISM: Artificial Sequence
```

```
<220> FEATURE:
<223> OTHER INFORMATION: aptamer

<400> SEQUENCE: 6
gggtttggtt tgggacgggg accagatttt cagcttcact cgtgg           45

<210> SEQ ID NO 7
<211> LENGTH: 45
<212> TYPE: DNA
<213> ORGANISM: Artificial Sequence
<220> FEATURE:
<223> OTHER INFORMATION: aptamer

<400> SEQUENCE: 7
gtgatacgta ggtagtggtg tgggtcctct ttgcacctta tggtc           45

<210> SEQ ID NO 8
<211> LENGTH: 45
<212> TYPE: DNA
<213> ORGANISM: Artificial Sequence
<220> FEATURE:
<223> OTHER INFORMATION: aptamer

<400> SEQUENCE: 8
ggggtgctcg gggtcgcagt cggtgcccgc ttgtcacaga tcagc           45

<210> SEQ ID NO 9
<211> LENGTH: 45
<212> TYPE: DNA
<213> ORGANISM: Artificial Sequence
<220> FEATURE:
<223> OTHER INFORMATION: aptamer

<400> SEQUENCE: 9
tggtgtaatc agcctaggag tgggtcgtga caggttgtat atctc           45

<210> SEQ ID NO 10
<211> LENGTH: 47
<212> TYPE: DNA
<213> ORGANISM: Artificial Sequence
<220> FEATURE:
<223> OTHER INFORMATION: aptamer

<400> SEQUENCE: 10
gttgcactgt gcggccgagc tgccccctgg tttgtgaata ccctggg         47

<210> SEQ ID NO 11
<211> LENGTH: 45
<212> TYPE: DNA
<213> ORGANISM: Artificial Sequence
<220> FEATURE:
<223> OTHER INFORMATION: aptamer

<400> SEQUENCE: 11
gcgtgtgtgt tagcgacgag ttggggcaac gatagtcata tgact           45

<210> SEQ ID NO 12
<211> LENGTH: 45
<212> TYPE: DNA
<213> ORGANISM: Artificial Sequence
<220> FEATURE:
<223> OTHER INFORMATION: aptamer

<400> SEQUENCE: 12
gcgagggcca acggtggtta cgtcgctacg gcgctactgg ttgat           45
```

<210> SEQ ID NO 13
<211> LENGTH: 45
<212> TYPE: DNA
<213> ORGANISM: Artificial Sequence
<220> FEATURE:
<223> OTHER INFORMATION: aptamer

<400> SEQUENCE: 13
aaaggaggca tggtctctgc taagccatcc tacctatact gaggc            45

<210> SEQ ID NO 14
<211> LENGTH: 45
<212> TYPE: DNA
<213> ORGANISM: Artificial Sequence
<220> FEATURE:
<223> OTHER INFORMATION: aptamer

<400> SEQUENCE: 14
ttgggcatga gttggtgatg cgggtttcga ttacgggtta ctgcg            45

<210> SEQ ID NO 15
<211> LENGTH: 45
<212> TYPE: DNA
<213> ORGANISM: Artificial Sequence
<220> FEATURE:
<223> OTHER INFORMATION: aptamer

<400> SEQUENCE: 15
gcgctctacc gccaggctac tcttggagag tcttttgggc tcttg            45

<210> SEQ ID NO 16
<211> LENGTH: 45
<212> TYPE: DNA
<213> ORGANISM: Artificial Sequence
<220> FEATURE:
<223> OTHER INFORMATION: aptamer

<400> SEQUENCE: 16
gaaaggctgt ttgcgcgcga gtctgtaaga tgtgcactga tcggt            45

<210> SEQ ID NO 17
<211> LENGTH: 45
<212> TYPE: DNA
<213> ORGANISM: Artificial Sequence
<220> FEATURE:
<223> OTHER INFORMATION: aptamer

<400> SEQUENCE: 17
gaaatagtgc tggctcttca tccgtcggtt gtgtgagggg tagtg            45

<210> SEQ ID NO 18
<211> LENGTH: 45
<212> TYPE: DNA
<213> ORGANISM: Artificial Sequence
<220> FEATURE:
<223> OTHER INFORMATION: aptamer

<400> SEQUENCE: 18
gatgaactaa tcgtgcgcct cgggtgggtt tcctgctgca tccat            45

<210> SEQ ID NO 19
<211> LENGTH: 45
<212> TYPE: DNA
<213> ORGANISM: Artificial Sequence
<220> FEATURE:
<223> OTHER INFORMATION: aptamer

```
<400> SEQUENCE: 19
tgagggcagg ccttagtatt ctgcctctta gaaaggcagg tgcgg          45

<210> SEQ ID NO 20
<211> LENGTH: 45
<212> TYPE: DNA
<213> ORGANISM: Artificial Sequence
<220> FEATURE:
<223> OTHER INFORMATION: aptamer

<400> SEQUENCE: 20
ctacctgcta ttcactgact ttcgtcgctt gtttcacagt gggac          45

<210> SEQ ID NO 21
<211> LENGTH: 45
<212> TYPE: DNA
<213> ORGANISM: Artificial Sequence
<220> FEATURE:
<223> OTHER INFORMATION: aptamer

<400> SEQUENCE: 21
caatttgcaa tttgggtatg tcattattag cgttatttga ctcat          45

<210> SEQ ID NO 22
<211> LENGTH: 45
<212> TYPE: DNA
<213> ORGANISM: Artificial Sequence
<220> FEATURE:
<223> OTHER INFORMATION: aptamer

<400> SEQUENCE: 22
attcaagtcc atcttaccgg ttgtgctcct cctgtgctac ttact          45

<210> SEQ ID NO 23
<211> LENGTH: 45
<212> TYPE: DNA
<213> ORGANISM: Artificial Sequence
<220> FEATURE:
<223> OTHER INFORMATION: aptamer

<400> SEQUENCE: 23
ggccgtgttc ggacggtttc atgctctatg agggcccttt accct          45

<210> SEQ ID NO 24
<211> LENGTH: 45
<212> TYPE: DNA
<213> ORGANISM: Artificial Sequence
<220> FEATURE:
<223> OTHER INFORMATION: aptamer

<400> SEQUENCE: 24
cagttgaggt cccgatttca cacgtatatc aggacattta tctga          45

<210> SEQ ID NO 25
<211> LENGTH: 45
<212> TYPE: DNA
<213> ORGANISM: Artificial Sequence
<220> FEATURE:
<223> OTHER INFORMATION: aptamer

<400> SEQUENCE: 25
gctgtagatc tatgggtggt tgcctgttct ggtttccatc gattt          45

<210> SEQ ID NO 26
```

```
<211> LENGTH: 46
<212> TYPE: DNA
<213> ORGANISM: Artificial Sequence
<220> FEATURE:
<223> OTHER INFORMATION: aptamer

<400> SEQUENCE: 26
gccttgtttt gcattgtatg cacgtacgtg gggtgctgcg tcagag         46

<210> SEQ ID NO 27
<211> LENGTH: 45
<212> TYPE: DNA
<213> ORGANISM: Artificial Sequence
<220> FEATURE:
<223> OTHER INFORMATION: aptamer

<400> SEQUENCE: 27
aacgcatagt ttcgggaatt ctacatgagc acgcccatta ccccg          45

<210> SEQ ID NO 28
<211> LENGTH: 45
<212> TYPE: DNA
<213> ORGANISM: Artificial Sequence
<220> FEATURE:
<223> OTHER INFORMATION: aptamer

<400> SEQUENCE: 28
gctagtacgc gttgttctgc agattatttt tgcgagtttg ttcgt          45

<210> SEQ ID NO 29
<211> LENGTH: 88
<212> TYPE: DNA
<213> ORGANISM: Artificial Sequence
<220> FEATURE:
<223> OTHER INFORMATION: random ssDNA library for E.coli
<220> FEATURE:
<221> NAME/KEY: misc_feature
<222> LOCATION: (20)..(64)
<223> OTHER INFORMATION: n is a, c, g, or t

<400> SEQUENCE: 29
gcaatggtac ggtacttccn nnnnnnnnnn nnnnnnnnnn nnnnnnnnnn nnnnnnnnnn    60
nnnncaaaag tgcacgctac tttgctaa                                       88

<210> SEQ ID NO 30
<211> LENGTH: 19
<212> TYPE: DNA
<213> ORGANISM: Artificial Sequence
<220> FEATURE:
<223> OTHER INFORMATION: primerF

<400> SEQUENCE: 30
gcaatggtac ggtacttcc                                       19

<210> SEQ ID NO 31
<211> LENGTH: 24
<212> TYPE: DNA
<213> ORGANISM: Artificial Sequence
<220> FEATURE:
<223> OTHER INFORMATION: primerR

<400> SEQUENCE: 31
ttagcaaagt agcgtgcact tttg                                 24
```

SINGLE-STRANDED NUCLEIC ACID APTAMERS SPECIFICALLY BINDING TO *E. COLI*

CROSS-REFERENCE TO RELATED APPLICATIONS

This application claims the benefit of Korean Patent Application No. 10-2012-0086395, filed on Aug. 7, 2012, in the Korean Intellectual Property Office, the disclosure of which is incorporated herein in its entirety by reference.

BACKGROUND

1. Field

The present disclosure relates to single-stranded nucleic acid aptamers specifically binding to *Escherichia coli* (*E. coli*) and methods for detecting *E. coli* using the same.

2. Description of the Related Art

To identify existence of harmful microorganisms in a water system, current practice involves detection of total coliforms present in the water, indicated by an index number. With regards to drinking water, existence of coliforms is measured based on the ability of degrading lactose. However, experimental methods of measuring the existence of coliforms are very complicated to require long experimental turnaround time (over 4 days), and also has high error rate and inaccuracy since the results are calculated based on statistical table. Therefore, a highly accurate *E. coli* monitoring sensor system for real-time monitoring of microorganism contamination of a water system due to pathogenic microorganism existence is required. In particular, securing of a receptor that recognizes *E. coli* with high specificity is essential for development of a highly sensitive and stable *E. coli* monitoring system.

Aptamer is a single-stranded nucleic acid with high specificity and affinity for various target substances. The related art sensor technologies for diagnosing diseases or for detecting harmful microorganisms mostly rely on immunological analysis using antibodies. Recent studies have been relying upon biosensor technology, wherein aptamers of high specificity and affinity for target substances are used in diagnosing diseases. Various chemical functional groups may be given to terminals of aptamers, and the specificity and affinity of aptamers may be maximized during a procedure of being selected in vitro. An aptamer may be mass-produced with high-purity and low-cost through chemical synthesis, and may be stored under room temperature for extended periods, as aptamers are thermally stable. In addition, aptamers may be enhanced with respect to their specificity for target substances by performing a counter selection on various materials which have a similar structure with the target or are largely present in actual samples.

Therefore, the present disclosure provides a simple, quick and accurate method of detecting the presence of *E. coli* within a water system by incorporating single-stranded nucleic acid aptamers specifically binding to *E. coli*.

SUMMARY

Provided are single-stranded nucleic acid aptamers that specifically bind to *E. coli*.

Provided are methods for detecting *E. coli* from a sample using single-stranded nucleic acid aptamers specifically binding to *E. coli*.

Provided are *E. coli* detection kits and *E. coli* detection sensors that include single-stranded nucleic acid aptamers specifically binding to *E. coli*.

Additional aspects will be set forth in part in the description which follows and, in part, will be apparent from the description, or may be learned by practice of the presented embodiments.

According to an aspect of the present invention, a single-stranded nucleic acid aptamer specifically binding to *E. coli* includes deoxyribonucleic acid (DNA), ribonucleic acid (RNA), peptide nucleic acid (PNA) and any combinations thereof. The terminology "aptamer" is a single-stranded nucleic molecule that has a stable 3-dimensional structure by itself and is characterized by being able to bind to a target molecule with high affinity and specificity. The aptamer may have a nucleotide sequence of SEQ ID NO: 1 to 28 or combinations thereof, for example, SEQ ID NO: 1, 2, 10, 12 or combinations thereof.

The aptamer may include a detectable label attached thereto. The detectable label may be a moiety that may be detected by detection methods known in the art. For example, the detectable marker may be an optical label, an electrochemical label, a radioisotope or combinations thereof. The label may be attached to a certain base or certain structure of an aptamer, for example, a certain site of a hairpin-loop structure or a 3' end or a 5' end of an aptamer.

The optical label may be, for example, a fluorescent substance. The fluorescent substance may be chosen from the group consisting of fluorescein, 6-FAM, rhodamine, Texas Red, tetramethylrhodamine, carboxyrhodamine, carboxyrhodamine 6G, carboxyrhodol, carboxyrhodamine 110, Cascade Blue, Cascade Yellow, Comarin, Cy2 (cyanine 2), Cy3, Cy3.5, Cy5, Cy5.5, Cy-chrome, phycoerythrin, PerCP (peridinine chlorophyl-a protein), PerCP-Cy5.5, JOE (6-carboxy-4',5'-dichloro-2',7'-dimethoxyfluorescein), NED, ROX (5-(and-6)-carboxy-X-rhodamine), HEX, Lucifer Yellow, Marina Blue, Oregon Green 488, Oregon Green 500, Oregon Green 514, Alexa Fluor, 7-amino-4-methylcomarin-3-acetate, BODIPY FL, BODIPY FL-Br 2, BODIPY 530/550, their conjugates and mixture thereof. For example, the fluorescent substance may be fluorescein, Cy3 or Cy5.

Also, the optical label may be a pair of fluorescence resonance energy transfers (FRET) that include donor fluorophore and acceptor fluorophore separated by an appropriate distance in which the fluorescence of the donor is inhibited by the acceptor. The donor fluorophore may include FAM, TAMRA, VIC, JOE, Cy3, Cy5 and Texas Red. The acceptor fluorophore may be selected such that excitation spectrum thereof overlaps emission spectrum of the donor. Also, the acceptor may be a non-fluorescent acceptor that quenches donors of broad range. Other examples of donor-acceptor FRET pair are known in the art.

The electrochemical label may include electrochemical labels known in the art. For example, the electrochemical label may be methylene blue.

According to another aspect of the present invention, a method for detecting *E. coli* includes: contacting a sample with a single-stranded nucleic acid aptamer which includes DNA, RNA, PNA or combinations thereof and binds specifically to *E. coli* to form an *E. coli-aptamer* complex; measuring a signal from the *E. coli-aptamer* complex; and identifying a presence or concentration of *E. coli* within the sample based on the measured signal.

In the above method, the contact between the sample and the aptamer may be performed in a reacting solution. For example, the contact may be performed in a reacting solution that includes a composition of salt that enables good binding between the aptamer and *E. coli* and a component that prevents nonspecific binding. The component preventing the nonspecific binding may include, for example, salmon sperm DNA, BSA and/or Tween-20. The reaction temperature may be, for example, about 5° C. to about 35° C., about 10° C. to about 30° C., about 15° C. to about 25° C., or about 20° C. to about 25° C. The reaction time may be, for example, over about a 1 hour, about 10 minutes to about 60 minutes, about 20 minutes to about 60 minutes, about 30 minutes to about 50 minutes, or about 40 minutes to about 50 minutes. The aptamer may have a nucleotide sequence that includes SEQ ID NO: 1 to 28 or any combinations thereof, for example, SEQ ID NO: 1, 2, 10, 12 or any combinations thereof. The aptamer may have a detectable label attached thereto. The detectable label may be an optical label, an electrochemical label, a radioisotope or combinations thereof.

In the above method, the signal from E. coli-aptamer complex may be generated from the optical label, electrochemical label or combinations thereof. The optical label may be, for example, donor-acceptor FRET pair. The electrochemical label may be, for example, methylene blue.

In the above method, the identifying of an existence or concentration of E. coli within the sample may be performed via comparison with a control group. The control group may be an aptamer in a status not bound with E. coli. For example, if the label attached to the aptamer is a donor-acceptor FRET pair, the control group may be an aptamer in which a fluorescent signal of donor fluorophore is inhibited by the acceptor fluorophore. When E. coli-aptamer complex is formed, the fluorescent signal changes by having FRET efficiency reduced, and existence or concentration of E. coli may be identified from the signal change. For example, if the label attached to an aptamer is an electrochemical label, the control group may be the labeled aptamer fixed to an electrode. The electrochemical signal changes by having the electrochemical label being distant or close to the electrode, or separated from the aptamer due to structural change of the aptamer bound with E. coli, and existence or concentration of E. coli may be identified from the signal change.

The method may further include separating the E. coli-aptamer complex from a reactant that includes the sample and the aptamer. The separating may be performed after forming the E. coli-aptamer complex, before measuring the signal from the complex. The separating may be, for example, performed by a membrane filtration method or centrifugation method. Also, the separating may be performed by washing off the aptamer when the aptamer is bound to the electrode. The optical label attached to the aptamer may be fluorescent substances as mentioned above. For example, the fluorescent substance may be fluorescein, Cy3 or Cy5. The signal generated from the separated E. coli-aptamer complex may be measured by, for example, a fluorometry or radioisotope detecting method.

According to another aspect of the present invention, an E. coli detection kit includes a single-stranded nucleic acid aptamer including DNA, RNA, PNA or combinations thereof, specifically binding to E. coli.

In the above kit, the aptamer may have a nucleotide sequence of SEQ ID NO: 1 to 28 or combinations thereof, for example, SEQ ID NO: 1, 2, 10, 12 or combinations thereof. The aptamer may include a detectable label attached thereto. The detectable label may be, for example, an optical label, a radioisotope or combinations thereof.

The kit may further include substances known to be required in forming E. coli-aptamer complex. The kit may further include components required for stimulation of specific E. coli-aptamer complex formation or inhibition of non-specific E. coli-aptamer complex formation, for example, salmon sperm DNA, BSA and/or Tween-20. Also, the kit may further include manual written about method of identifying E. coli within samples with the aptamer.

According to another aspect of the present invention, an E. coli detection sensor includes a single-stranded nucleic acid aptamer including DNA, RNA, PNA or combinations thereof, specifically binding to E. coli.

In the above sensor, the aptamer may have nucleotide sequence of SEQ ID NO: 1 to 28 or combinations thereof, for example, SEQ ID NO: 1, 2, 10, 12 or combinations thereof. The aptamer may include a detectable label attached thereto. The detectable label may be an optical label, an electrochemical label, or combinations thereof. The sensor including the optical label may use, for example, FRET effect. The sensor including the electrochemical label may be based on principle of electrochemical signal changes performed by having the electrochemical label being distant or close to the electrode, or separated from the aptamer due to structural change of the aptamer bound with target substance.

The sensor may include a substrate with more than two of the aptamers fixed thereon, for example, be an array form. An array refers to a substrate with certain regions having numbers of specific molecules fixed thereon. The array may include a substrate and a fixation region that is formed on the substrate and includes aptamers capable of binding with E. coli. The aptamer may be covalently attached within the fixation region. The aptamer may further include a plurality of compounds with functional groups that may be covalently attached. The functional group may be any type as long as it is capable of attaching the aptamer to the substrate. For example, the functional group may be aldehyde, epoxy or amine group, and the compound may be siloxane with aldehyde, epoxy or amine group at the end. The material of the substrate may be, for example, glass, silicon, polypropylene and polyethylene.

BRIEF DESCRIPTION OF THE DRAWINGS

The above and other aspects and advantages of the present invention will become more apparent by describing in detail exemplary embodiments thereof with reference to the attached drawings in which.

DETAILED DESCRIPTION

Reference will now be made in detail to embodiments of the present invention, examples of which are illustrated in the accompanying drawings, wherein like reference numerals refer to the like elements throughout. In this regard, the present embodiments may have different forms and should not be construed as being limited to the descriptions set forth herein.

Example 1

Manufacture of a DNA Aptamer Specifically Binding to *E. coli*

**1. *E. coli* Cultivation**

Feces-originated *E. coli* KCTC2571 was cultured at 37° C. after inoculation in nutrient broth (beef extract 37%, pepton 63%, 8 g broth/L D.W, and pH 6.8). Once the concentration of the *E. coli* reached $10^8$ CFU/ml, culture media was removed by washing it off 3 times with phosphate buffered saline (PBS). The *E. coli* cells were then suspended in a binding buffer (1×PBS, 0.1 mg/ml salmon sperm DNA, 1% BSA, and 0.05% Tween-20).

2. Manufacture of Random Single-Stranded DNA (ssDNA) Library

A ssDNA library consisting of the following single-stranded DNA oligonucleotide was synthesized. As a result, a random ssDNA library having $10^{15}$ different oligonucleotides was synthesized.

```
                                              (SEQ ID NO: 29)
5'-GCAATGGTACGGTACTTCC-N45-CAAAAGTGCACGCTACTTT
GCTAA-3'
```

The underlined sites in the above represent the fixed sequences where the following primer pairs are annealed, and $N_{45}$ represents random existence of adenine (A), guanine (G), thymine (T), and cytosine (C) bases in each site.

3. Whole-Cell SELEX

The random ssDNA library having $10^{15}$ different oligonucleotides was dissolved in a binding buffer (1×PBS, 0.1 mg/ml salmon sperm DNA, 1% BSA, 0.05% Tween-20) and heated for 5 minutes at 95° C. Temperature was then immediately reduced to 4° C. and held for 10 minutes, and the random ssDNA library was mixed with 1 mL of *E. coli* suspension ($10^7$ cells) for an hour at room temperature. The *E. coli*/ssDNA complex was separated from the solution using a centrifuge at 13,000 rpm for 10 minutes. The separated *E. coli*/ssDNA complex was suspended in PBS buffer and the procedures were repeated 3 times. Finally, the *E. coli*/ssDNA complex was resuspended in sterilized distilled water. The resuspension was heated for 10 minutes at 95° C. and then held at 4° C. for 10 minutes in order to separate ssDNA from *E. coli*/ssDNA complex. The separated ssDNA was collected by using the centrifuge set at 13,000 rpm for 10 minutes.

The amount of the ssDNA selected from the procedure was amplified through polymerase chain reaction (PCR). The forward primer was a primer labeled with fluorescein at its 5'-end and the reverse primer was a primer labeled with biotin at its 5'-end. This was done to separate the dsDNA, the product of PCR, into a single-stranded DNA.

```
    Forward:
                                              (SEQ ID NO: 30)
    5'-fluorescein-GCAATGGTACGGTACTTCC-3'

Reverse:
                                              (SEQ ID NO: 31)
    5'-biotin-TTAGCAAAGTAGCGTGCACTTTTG-3'
```

Figure 1:
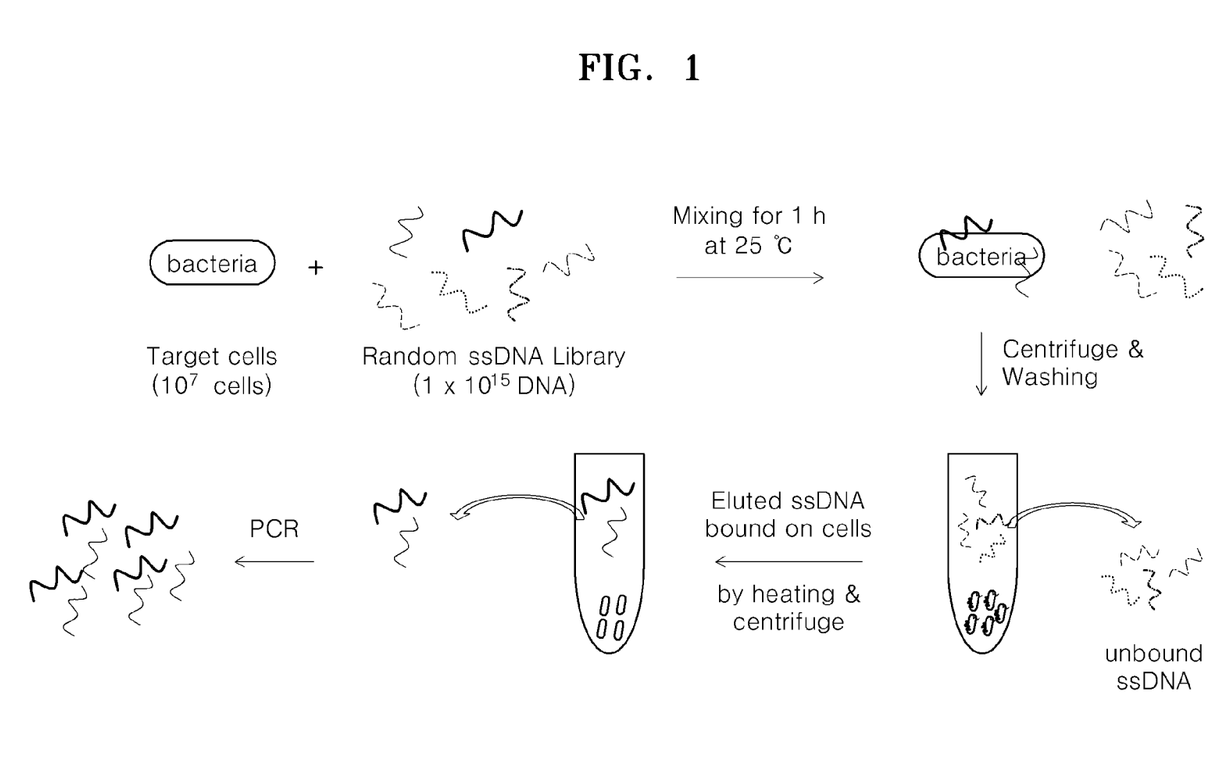
FIG. 1 is a schematic view of a Bacteria Cell-SELEX method to select a DNA aptamer that may specifically bind to E. coli.
Figure 2:
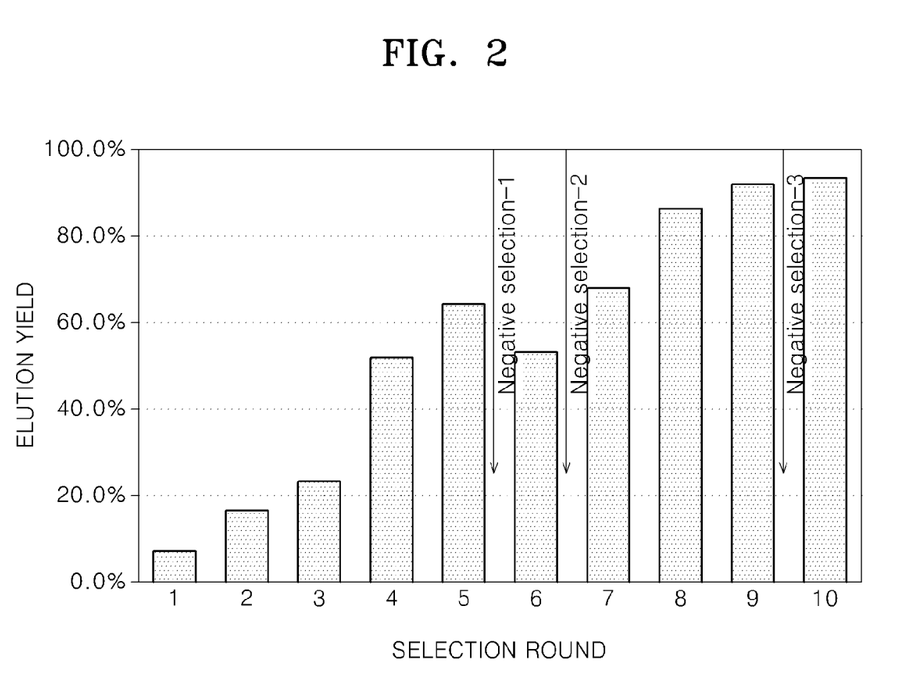
FIG. 2 is a percentage graph of a single-stranded DNA that binds to E. coli among the single-stranded DNA library used in each selection round.
Figure 3A:
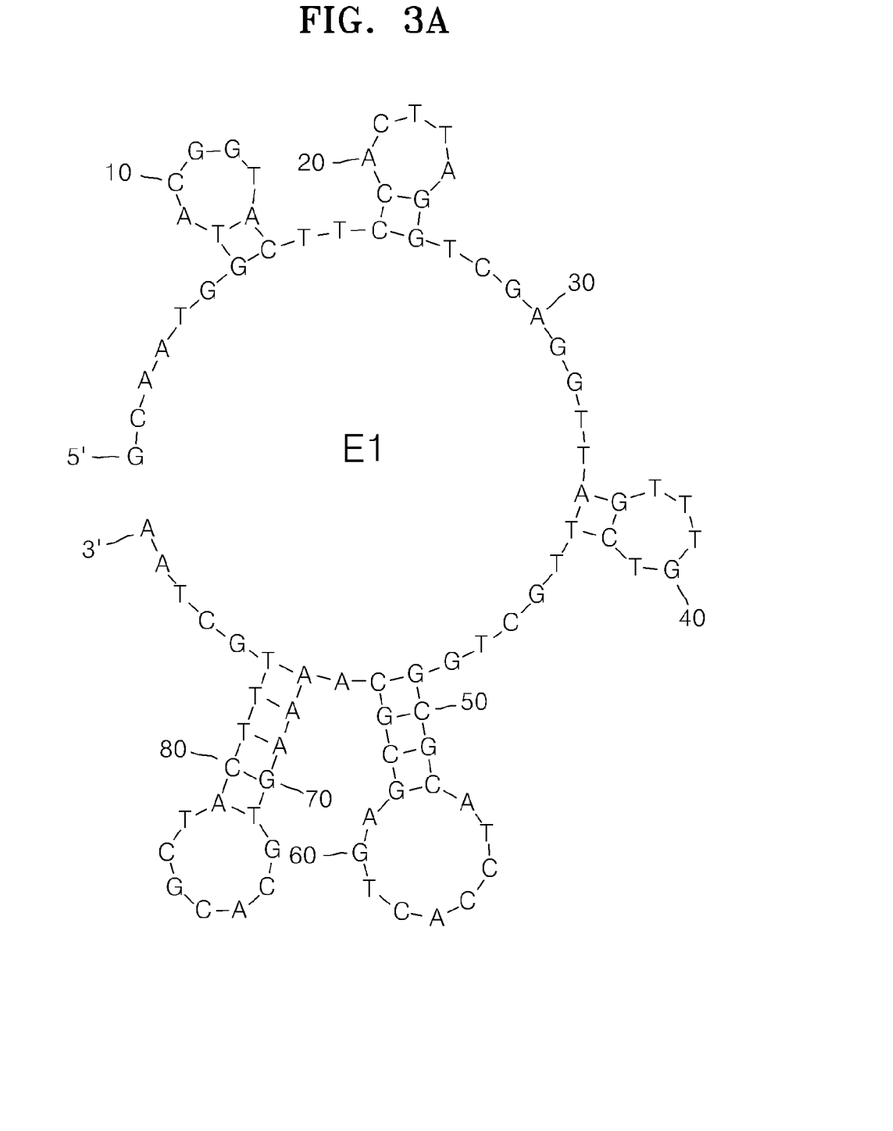
FIG. 3A to 3D are schematic views of an predicted secondary structure for a DNA aptamer that specifically binds to E. coli, based on an mfold program.
Figure 3B:
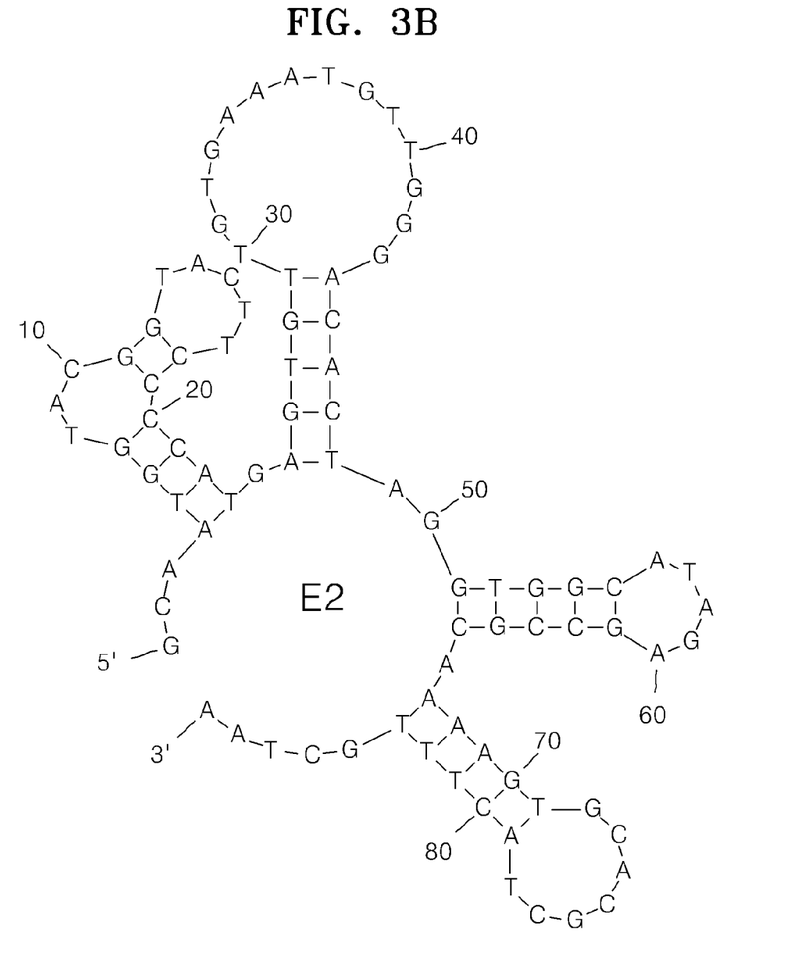
Figure 3C:
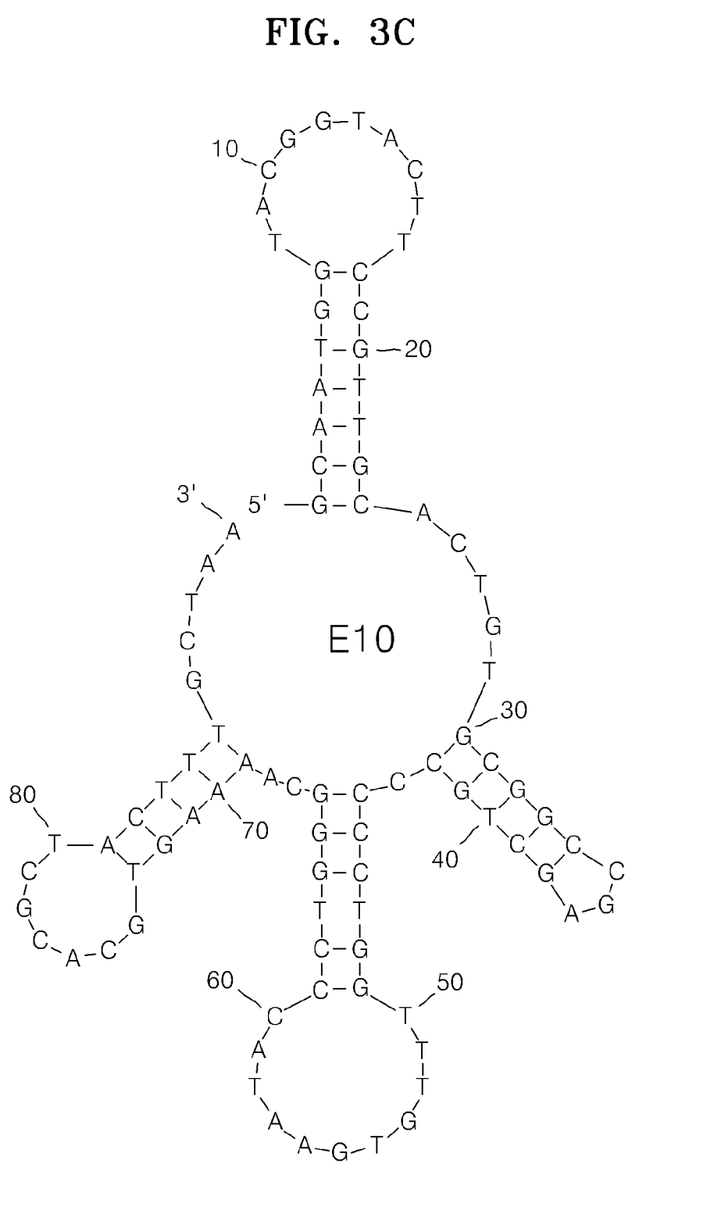
Figure 3D:
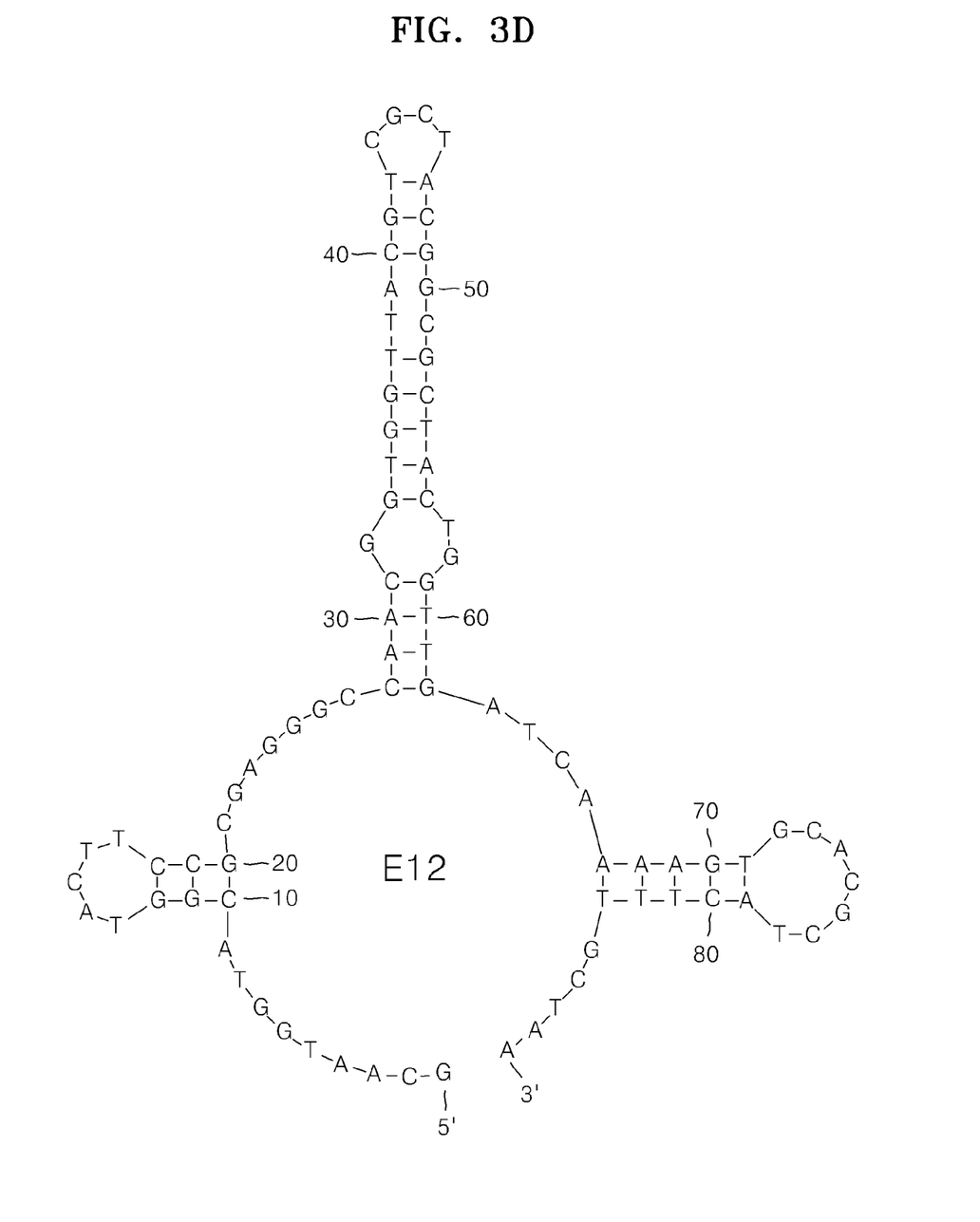

PCR was performed under the conditions of 95° C. (30 seconds), 56.3° C. (30 seconds) and 72° C. (10 seconds), with a total of 25 µl volume obtained by mixing 10 µl of ssDNA (which is approximately 100 ng), 1.25 µl of each primers with 10 µM, and 12.5 µl of PCR master mix, and the number of repeating cycle was 10. Electrophoresis was performed in 2% agarose gel to identify the proper performance of PCR. Afterwards, the PCR product was purified using a PCR purification kit (MinElute PCR Purification kit by QIAGEN). 100 µl of the purified PCR product was mixed with magnetic beads coated with 50 µl of avidin (Dynabeads MyOne™ Streptavidin, Invitrogen), allowed to react for 10 minutes at room temperature, and then washed with 1 ml of PBS buffer using a magnet. 500 µl of 200 mM sodium hydroxide (NaOH) was added to the mixture and the mixture was allowed to react for 5 minutes in order to denature dsDNA into ssDNA. Biotin-attached ssDNA was removed from the reacting solution using a magnet, and fluorescein-attached ssDNA was collected. The collected fluorescein-attached ssDNA was purified/condensed using the PCR purification kit and the concentration was analyzed. Concentrated ssDNA was used for the next round's selection procedure, wherein selection and amplification procedures were repeated multiple times as shown in FIG. 2. After completing a total of 10 selection procedures, it was ultimately found that 93.7% of ssDNA among the ssDNA mixed with *E. coli* were bound with *E. coli*.

Among SELEX procedures, a counter selection procedure was performed 3 times in total after 5th, 6th and 9th selection procedures using 4 types of bacteria (*Klebsiella pneumoniae, Citrobacter freundii, Enterobacter aerogenes, Staphylococcus epidermidis*) that are vastly found with target *E. coli* in water systems such as sewage. The methods and conditions of this counter selection procedure were equal to the prior selection procedure, however in the counter selection procedure, ssDNAs binding to the bacteria were removed, and ssDNAs not binding to the bacteria were collected, amplified and used for the next stage of the selection procedure.

The finally obtained ssDNAs were subjected to PCR using the primer pairs and were cloned using a cloning kit (TOPO TA cloning kit). Plasmids were extracted from each colony, and base sequence analysis was performed, wherein a total of 28 different base sequences were obtained. The following Table 1 consists of the total 28 ssDNA base sequences selected from SELEX method.

TABLE 1

| | Random Site Base Sequence |
|---|---|
| E1 | 5'-ACTTAGGTCGAGGTTAGTTTGTCTTGCTGGCGCATCCACT GAGCG-3' (SEQ ID NO: 1) |
| E2 | 5'-CCATGAGTGTTGTGAAATGTTGGGACACTAGGTGGCATAG AGCCG-3' (SEQ ID NO: 2) |
| E3 | 5'-AGGTTCGAACGTCATGATGCCCCAGTTGACATCATTCAAA CGGAT-3' (SEQ ID NO: 3) |
| E4 | 5'-TGTTCGTCGCCGCGTGGCCTGGGGGGAGGGTTGCTTGATT GCCTA-3' (SEQ ID NO: 4) |
| E5 | 5'-CCACTGCGGTTGGCGCGCCGACCTTTCTGTTAGCCTGAAA CGCAG-3' (SEQ ID NO: 5) |
| E6 | 5'-GGGTTTGGTTTGGGACGGGGACCAGATTTTCAGCTTCACT CGTGG-3' (SEQ ID NO: 6) |
| E7 | 5'-GTGATACGTAGGTAGTGGTGTGGGTCCTCTTTGCACCTTA TGGTC-3' (SEQ ID NO: 7) |

TABLE 1-continued

| | Random Site Base Sequence |
|---|---|
| E8 | 5'-GGGGTGCTCGGGGTCGCAGGTCGGTGCCCGCTTGTCACAG<br>ATCAGC-3'<br>(SEQ ID NO: 8) |
| E9 | 5'-TGGTGTAATCAGCCTAGGAGTGGGTCGTGACAGGTTGTAT<br>ATCTC-3'<br>(SEQ ID NO: 9) |
| E10 | 5'-GTTGCACTGTGCGGCCGAGCTGCCCCCTGGTTTGTGAATA<br>CCCTGGG-3'<br>(SEQ ID NO: 10) |
| E11 | 5'-GCGTGTGTGTTAGCGACGAGTTGGGGCAACGATAGTCATA<br>TGACT-3'<br>(SEQ ID NO: 11) |
| E12 | 5'-GCGAGGGCCAACGGTGGTTACGTCGCTACGGCGCTACTGG<br>TTGAT-3'<br>(SEQ ID NO: 12) |
| E13 | 5'-AAAGGAGGCATGGTCTCTGCTAAGCCATCCTACCTATACT<br>GAGGC-3'<br>(SEQ ID NO: 13) |
| E14 | 5'-TTGGGCATGAGTTGGTGATGCGGGTTTCGATTACGGGTTA<br>CTGCG-3'<br>(SEQ ID NO: 14) |
| E15 | GCGCTCTACCGCCAGGCTACTCTTGGAGAGTCTTTTGGGCTCT<br>TG-3'<br>(SEQ ID NO: 15) |
| E16 | 5'-GAAAGGCTGTTTGCGCGCGAGTCTGTAAGATGTGCACTGA<br>TCGGT-3'<br>(SEQ ID NO: 16) |
| E17 | 5'-GAAATAGTGCTGGCTCTTCATCCGTCGGTTGTGTGAGGGG<br>TAGTG-3'<br>(SEQ ID NO: 17) |
| E18 | 5'-GATGAACTAATCGTGCGCCTCGGGTGGGTTTCCTGCTGCA<br>TCCAT-3'<br>(SEQ ID NO: 18) |
| E19 | 5'-TGAGGGCAGGCCTTAGTATTCTGCCTCTTAGAAAGGCAGG<br>TGCGG-3'<br>(SEQ ID NO: 19) |
| E20 | 5'-CTACCTGCTATTCACTGACTTTCGTCGCTTGTTTCACAGT<br>GGGAC-3'<br>(SEQ ID NO: 20) |
| E21 | 5'-CAATTTGCAATTTGGGTATGTCATTATTAGCGTTATTTGA<br>CTCAT-3'<br>(SEQ ID NO: 21) |
| E22 | 5'-ATTCAAGTCCATCTTACCGGTTGTGCTCCTCCTGTGCTAC<br>TTACT-3'<br>(SEQ ID NO: 22) |
| E23 | 5'-GGCCGTGTTCGGACGGTTTCATGCTCTATGAGGGCCCTTT<br>ACCCT-3'<br>(SEQ ID NO: 23) |
| E24 | 5'-CAGTTGAGGTCCCGATTTCACACGTATATCAGGACATTTA<br>TCTGA-3'<br>(SEQ ID NO: 24) |
| E25 | 5'-GCTGTAGATCTATGGGTGGTTGCCTGTTCTGGTTTCCATC<br>GATTT-3'<br>(SEQ ID NO: 25) |
| E26 | 5'-GCCTTGTTTTGCATTGTATGCACGTACGTGGGGTGCTGCG<br>TCAGAG-3'<br>(SEQ ID NO: 26) |
| E27 | 5'-AACGCATAGTTTCGGGAATTCTACATGAGCACGCCCATTA<br>CCCCG-3'<br>(SEQ ID NO: 27) |
| E28 | 5'-GCTAGTACGCGTTGTTCTGCAGATTATTTTTGCGAGTTTG<br>TTCGT-3'<br>(SEQ ID NO: 28) |

Example 2

Analysis of Coherence and Specificity for *E. coli*

Secondary structure analysis was performed using an mfold program (http://mfold.rna.albany.edu/?q=mfold; Zuker, M. Nucleic Acids Res. 2003, 31, 3406) among 28 ssDNAs with their base sequence analyzed. As a result of the analysis, approximately 10 types of ssDNAs were expected of high coherence for *E. coli*, and coherence and specificity of the ssDNAs for *E. coli* were analyzed for verification.

First, for coherence analysis for *E. coli*, *E. coli* KCTC2571 was cultured at 37° C. after inoculation in nutrient broth (beef extract 37%, pepton 63%, 8 g broth/L in distilled water, and pH 6.8). After the concentration of *E. coli* reached $10^8$ CFU/ml, culture media was removed by washing it off 3 times with PBS buffer, and the remaining *E. coli* was then suspended in a binding buffer (1×PBS, 0.1 mg/ml salmon sperm DNA, 1% BSA, 0.05% Tween-20). 100 μl of *E. coli* ($10^7$ cells) was mixed with 100 μl of fluorescently labeled ssDNA in various concentrations (0, 5, 12.5, 25, 50, 125, and 250 nM as final concentration) and allowed to react for 45 minutes at room temperature. After reaction, ssDNAs not bound to *E. coli* were removed by washing the product of the reaction twice with PBS buffer, followed by a fluorescence intensity analysis of *E. coli*/ssDNA complex (Ex/Em=494 nm/521 nm, slit width: 10 nm, exposure time: 1 s) using a fluorescence spectrometer (LS50B, PerkinElmer Co., USA). Fluorescence intensity in each ssDNA concentration condition was plotted using a nonlinear regression method and a single-region saturation ligand binding method of a SigmaPlot program involving the equation $F=B_{max}*C/(Kd+C)$, wherein F represents fluorescence intensity, $B_{max}$ represents maximum binding location, Kd is a dissociation constant, and C is a concentration of ssDNA.

Figure 4:
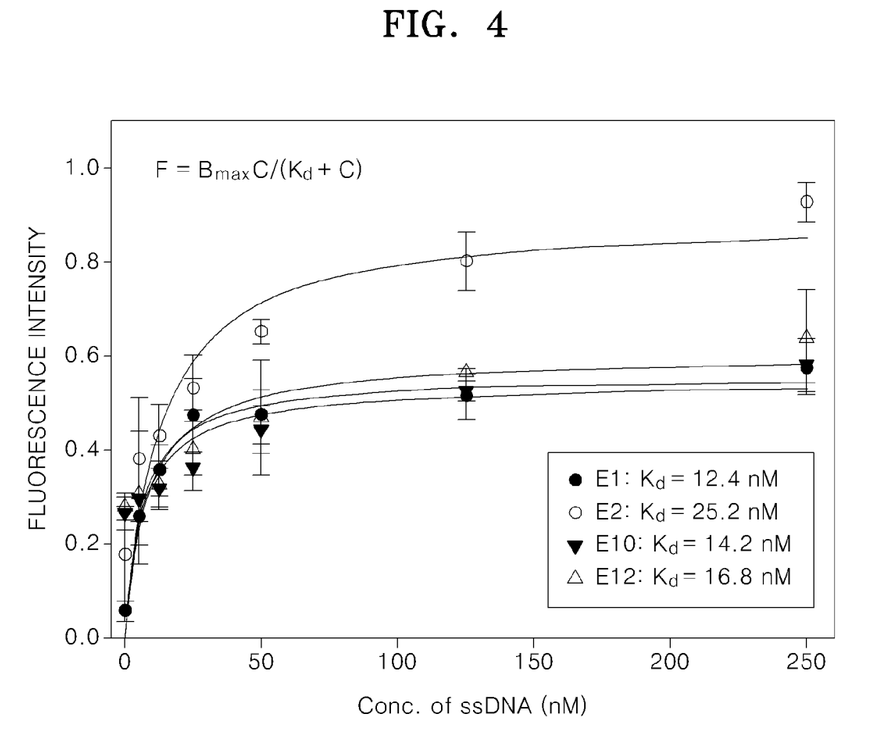
FIG. 4 is a coherence analysis result graph for a DNA aptamer that specifically binds to E. coli.

As a result of the above coherence analysis, 4 types of ssDNAs showing high affinity to *E. coli* is shown in FIG. 4. The coherence of the determined 4 types of ssDNAs showing high affinity to *E. coli* is as follows, wherein Kd is a dissociation constant:

E1 (Kd=12.4 nM), E2 (Kd=25.2 nM), E10 (Kd=14.2 nM), and E12 (Kd=16.8 nM).

Figure 5:
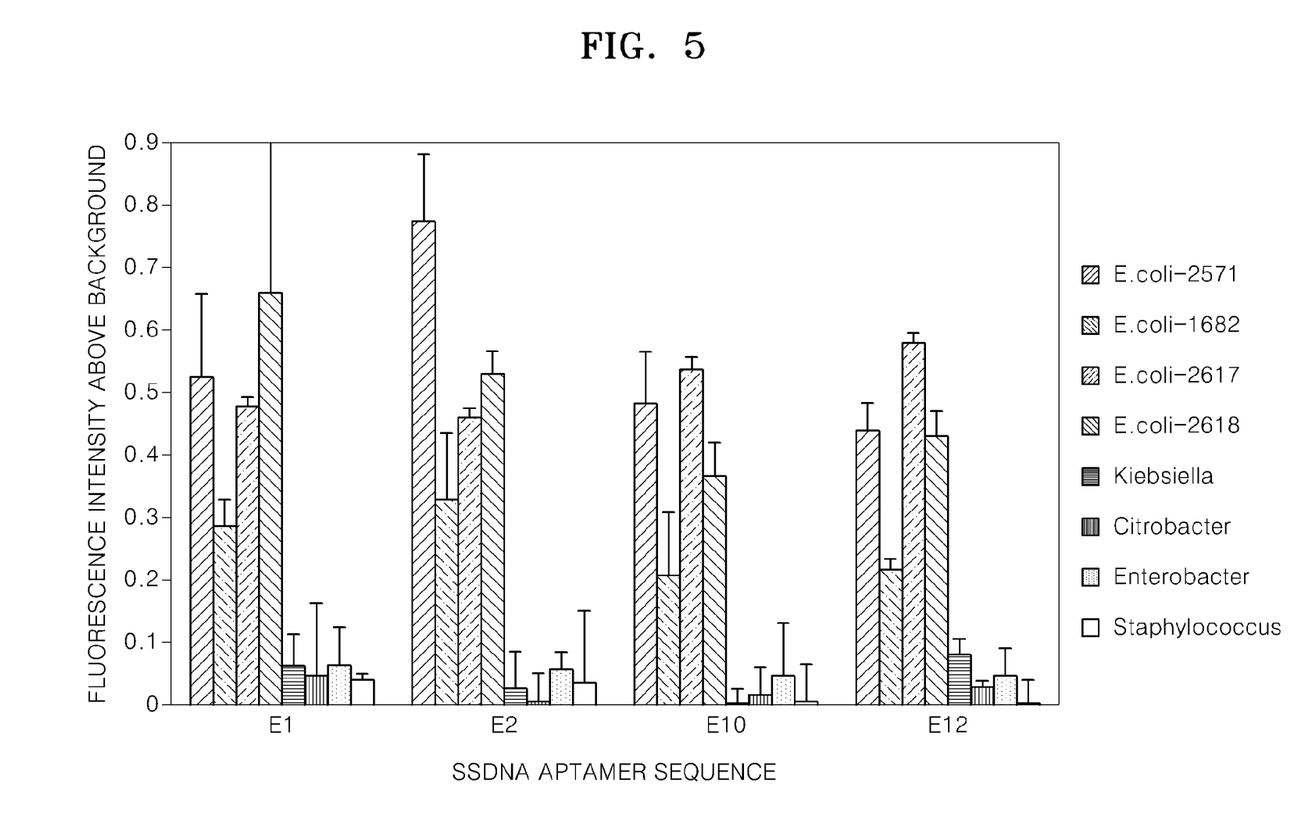
FIG. 5 is a specificity analysis result graph for a DNA aptamer that specifically binds to E. coli.

Selectivity analysis for the 4 types of ssDNAs was performed using 4 other types of bacteria (*Klebsiella pneumoniae, Citrobacter freundii, Enterobacter aerogenes*, and *Staphylococcus epidermidis*) and *E. coli* types different from the target *E. coli* (KCTC1682, KCTC2617, and KCTC2618). The selectivity analysis was performed by mixing 100 μl of each bacteria (i.e. $10^7$ cells of each bacteria) with 100 μl of 500 nM ssDNA, allowing the mixtures to react for 45 minutes at room temperature, washing the products of the reactions with PBS buffer and comparing the final results by measuring fluorescence intensity of bacteria/ssDNA complex. As shown in FIG. 5, the 4 types of ssDNAs E1, E2, E10 and E12 all exhibited fluorescence intensity of less than 10% when mixed with *Klebsiella, Citrobacter, Enterobacter* and *Staphylococcus*, while exhibiting fluorescence intensity ranging from approximately 0.5× to 1× that of the target *E. coli* for *E. coli* types different from the target *E. coli* (KCTC1682, KCTC2617, KCTC2618).

According to the examples above, the existence and concentration of *E. coli* within a water system may be quickly and accurately detected by using the single-stranded nucleic acid aptamers specifically binding to *E. coli* of the present disclosure.

While this invention has been particularly shown and described with reference to exemplary embodiments thereof, it will be understood by those skilled in the art that various changes in form and details may be made therein without departing from the spirit and scope of the invention as defined by the appended claims.

What is claimed is:

1. A single-stranded nucleic acid aptamer comprising deoxyribonucleic acid (DNA), ribonucleic acid (RNA), peptide nucleic acid (PNA) and any combinations thereof, the single-stranded nucleic acid aptamer specifically binding to Escherichia coli (E. coli), wherein the single-stranded nucleic acid aptamer has a nucleotide sequence comprising SEQ ID NO: 1, 2, 10, 12 or combinations thereof.

2. The aptamer of claim 1, wherein the single-stranded nucleic acid aptamer has a detectable label attached thereto.

3. The aptamer of claim 2, wherein the detectable label is an optical label, an electrochemical label, a radioisotope or a combination thereof.

4. An E. coli detection kit comprising the single-stranded nucleic acid aptamer of claim 1 or 2.

5. The kit of claim 4, wherein the E. coli detection kit comprises a detectable label, wherein the detectable label comprises an optical label, a radioisotope or a combination thereof.

6. An E. coli detection sensor comprising the aptamer of claim 1 or 2.

7. The sensor of claim 6, further comprising a substrate with more than two aptamers fixed thereon.

8. A method for detecting E. coli, comprising:
   contacting a sample with the aptamer of any of claims 1, 3, and 4 to form an E. coli-aptamer complex;
   measuring a signal from the E. coli-aptamer complex; and
   identifying a presence or concentration of E. coli within the sample based on the measured signal.

9. The method of claim 8, wherein the identifying of the presence or concentration of E. coli within the sample is performed via comparison with a control group.

10. The method of claim 8, further comprising separating the E. coli-aptamer complex from a reactant, wherein the reactant includes the sample and the aptamer.

* * * * *